United States Patent
Linnenbach et al.

(10) Patent No.: US 6,645,498 B1
(45) Date of Patent: Nov. 11, 2003

(54) SOLUBLE VARIANTS OF TYPE I MEMBRANE PROTEINS, AND METHODS OF USING THEM

(75) Inventors: Alban J. Linnenbach, Philadelphia, PA (US); Hilary Koprowski, Wynnewood, PA (US); Dorothee Herlyn, Wynnewood, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 08/413,805

(22) Filed: Mar. 30, 1995

Related U.S. Application Data (62) Division of application No. 08/148,216, filed on Nov. 5, 1993, now abandoned, which is a continuation of application No. 07/778,232, filed on Oct. 18, 1991, now abandoned.

(51) Int. Cl.[7] .............................................. A61K 39/00
(52) U.S. Cl. ..................................... 424/185.1; 530/350
(58) Field of Search ................................ 530/350, 395; 424/185.1

(56) References Cited

U.S. PATENT DOCUMENTS

| | | | |
|---|---|---|---|
| 4,778,879 A | * 10/1988 | Mertlesmann et al. | 530/351 |
| 4,920,016 A | * 4/1990 | Allen et al. | 424/450 |
| 5,141,742 A | 8/1992 | Brown et al. | |
| 5,185,254 A | 2/1993 | Linnenbach | |

FOREIGN PATENT DOCUMENTS

| | | |
|---|---|---|
| EP | 326423 | 8/1989 |
| EP | 376 746 A2 | 7/1990 |
| WO | WO93/08298 | 4/1993 |

OTHER PUBLICATIONS

Lazar et al. Molecular and Cellular Biology 8(3):1247–1252 Mar. 1988.*

Burgess et al. The Journal of Cell Biology 111(5):2129–2138 Nov. 1990.*

J. Strand et al, "Molecular Cloning and Characterization of a Human Adenocarcinoma/Epithelial Cell Surface Antigen Complementary DNA", Cancer Res., 49:314–317

M. Perez et al, "Isolation and Characterization of a cDNA Encoding the KS1/4 Epithelial Carcinoma Marker", J. Immunol., 142(10):3662–3667 (May 15, 1989).

B. Simon et al, "Epithelial Glycoprotein is a Member of a Family of Epithelial Cell Surface Antigens Homologous to Nidogen, a Matrix Adhesion Protein", Proc. Natl. Acad. Sci. USA, 87:2755–2759 (Apr., 1990).

S. Szala et al, "Molecular Cloning of cDNA for the Carcinoma–Associated Antigen GA733–2", Proc. Natl. Acad. Sci. USA, 87:3542–3546 (May, 1990) [Szala I].

L. Pedraza et al, "The Myelin–Associated Glycoproteins: Membrane Disposition, Evidence of a Novel Disulfide Linkage between Immunoglobulin–like Domains, and Posttranslational Palmitylation", J. Cell Biol., 111(6):2651–2661 (Dec., 1990).

P. Johnson et al, "Synthesis of Soluble Myelin–Associated Glycoprotein in Insect and Mammalian Cells", Gene, 77: 287–296 (1989).

A. Ross et al, "Isolation and Characterization of a Carcinoma–Associated Antigen", Biochem. and Biophys. Res. Commun., 135(1):297–303 (Feb. 26, 1986).

S. Szala et al, "Molecular Cloning of cDNA for the Human Tumor–Associated Antigen CO–029 and Identification of Related Transmembrane Abtigens", Proc. Natl. Acad. Sci. USA, 87:6833–6837 (Sep., 1990) [Szala II].

R. Hussey et al, "A Soluble CD4 Protein Selectively Inhibits HIV Replication and Syncytium Formation", Nature, 331: 78–81 (Jan. 7, 1988).

N. Varki et al, "Antigens Associated with a Human Lung Adenocarcinoma Defined by Monoclonal Antibodies", Cancer research, 44:681–687 (Feb., 1984).

D. Herlyn et al, "Inhibition of Human Tumor Growth by IgG2A Monoclonal Antibodies Correlates with Antibody Density on Tumor Cells", J. Immunol., 134(2):1300–1304 (Feb., 1985).

A. Gennaro, Remington's Pharmaceutical Sciences, 18th Ed., Chapter 23, pp. 406, published by Mack Publishing Company (1990).

D. Herlyn et al, "Efficient Selection of Human Tumor Growth–Inhibiting Monoclonal Antibodies", J. Immunol. Methods, 73: 157–167 (1984) [Herlyn II].

D. Herlyn et al, "Initial Clincical Evaluation of Two Murine IgG2a Monoclonal Antibodies for Immunotherapy of Gastrointestinal Carcinoma", Am. J. Clin. Onocol., 14(5):371–378 (Oct., 1991) [Herlyn III].

C. Strassburg et al, "Baculovirus Recombinant Expressing a Secreted form of a Transmembrane Carcinoma–associated Antigen", Cancer Research, 52:815–821 (Feb. 15, 1992).

K. Deen et al, "A Soluble Form of CD4 (T4) Protein Inhibits AIDS Virus Infection", Nature, 331:82–81 (Jan., 1988).

* cited by examiner

Primary Examiner—Marianne P. Allen
(74) Attorney, Agent, or Firm—Howson and Howson (57) ABSTRACT

The present invention describes novel soluble variants of type I membrane protein GA733-2 and methods of making and using them. In addition, the present invention describes a method of converting type I membrane proteins into secretory proteins which may be used for active immunotherapy against carcinomas and as reagents in the detection of GA733-2 expression on tumor cells.

4 Claims, 5 Drawing Sheets

FIGURE 1 A

```
CCCAGGCCTC GCGCTGCCCG GCCGGCTCCT CGTGTCCCAC TCCCGGCGCA        50

CGCCCTCCCG CGAGTCCCGG GCCCCTCCCG CGCCCCTCTT CTCGGCGCGC       100

GCGCAGC ATG GCG CCC CCG CAG GTC CTC GCG TTC GGG CTT CTG      143
        Met Ala Pro Pro Gln Val Leu Ala Phe Gly Leu Leu
         1               5                  10

CTT GCC GCG GCG ACG GCG ACT TTT GCC GCA GCT CAG GAA GAA      185
Leu Ala Ala Ala Thr Ala Thr Phe Ala Ala Ala Gln Glu Glu
        15                  20                  25

TGT GTC TGT GAA AAC TAC AAG CTG GCC GTA AAC TGC TTT GTG      227
Cys Val Cys Glu Asn Tyr Lys Leu Ala Val Asn Cys Phe Val
                30                  35                  40

AAT AAT AAT CGT CAA TGC CAG TGT ACT TCA GTT GGT GCA CAA      269
Asn Asn Asn Arg Gln Cys Gln Cys Thr Ser Val Gly Ala Gln
                45                  50

AAT ACT GTC ATT TGC TCA AAG CTG GCT GCC AAA TGT TTG GTG      311
Asn Thr Val Ile Cys Ser Lys Leu Ala Ala Lys Cys Leu Val
 55                  60                  65

ATG AAG GCA GAA ATG AAT GGC TCA AAA CTT GGG AGA AGA GCA      353
Met Lys Ala Glu Met Asn Gly Ser Lys Leu Gly Arg Arg Ala
     70                  75                  80
```

FIGURE 1 B

```
AAA CCT GAA GGG GCC CTC CAG AAC AAT GAT GGG CTT TAT GAT     395
Lys Pro Glu Gly Ala Leu Gln Asn Asn Asp Gly Leu Tyr Asp
         85                  90                  95

CCT GAC TGC GAT GAG AGC GGG CTC TTT AAG GCC AAG CAG TGC     437
Pro Asp Cys Asp Glu Ser Gly Leu Phe Lys Ala Lys Gln Cys
            100                 105                 110

AAC GGC ACC TCC ACG TGC TGG TGT GTG AAC ACT GCT GGG GTC     479
Asn Gly Thr Ser Thr Cys Trp Cys Val Asn Thr Ala Gly Val
                115                 120

AGA AGA ACA GAC AAG GAC ACT GAA ATA ACC TGC TCT GAG CGA     521
Arg Arg Thr Asp Lys Asp Thr Glu Ile Thr Cys Ser Glu Arg
125                 130                 135

GTG AGA ACC TAC TGG ATC ATC ATT GAA CTA AAA CAC AAA GCA     563
Val Arg Thr Tyr Trp Ile Ile Ile Glu Leu Lys His Lys Ala
        140                 145                 150

AGA GAA AAA CCT TAT GAT AGT AAA AGT TTG CGG ACT GCA CTT     605
Arg Glu Lys Pro Tyr Asp Ser Lys Ser Leu Arg Thr Ala Leu
            155                 160                 165

CAG AAG GAG ATC ACA ACG CGT TAT CAA CTG GAT CCA AAA TTT     647
Gln Lys Glu Ile Thr Thr Arg Tyr Gln Leu Asp Pro Lys Phe
                170                 175                 180

ATC ACG AGT ATT TTG TAT GAG AAT AAT GTT ATC ACT ATT GAT     689
Ile Thr Ser Ile Leu Tyr Glu Asn Asn Val Ile Thr Ile Asp
                    185                 190
```

FIGURE 1 C

```
CTG GTT CAA AAT TCT TCT CAA AAA ACT CAG AAT GAT GTG GAC      731
Leu Val Gln Asn Ser Ser Gln Lys Thr Gln Asn Asp Val Asp
195             200                 205

ATA GCT GAT GTG GCT TAT TAT TTT GAA AAA GAT GTT AAA GGT      773
Ile Ala Asp Val Ala Tyr Tyr Phe Glu Lys Asp Val Lys Gly
    210             215                 220

GAA TCC TTG TTT CAT TCT AAG AAA ATG GAC CTG ACA GTA AAT      815
Glu Ser Leu Phe His Ser Lys Lys Met Asp Leu Thr Val Asn
        225             230                 235

GGG GAA CAA CTG GAT CTG GAT CCT GGT CAA ACT TTA ATT TAT      857
Gly Glu Gln Leu Asp Leu Asp Pro Gly Gln Thr Leu Ile Tyr
            240             245                 250

TAT GTT GAT GAA AAA GCA CCT GAA TTC TCA ATG CAG GGT CTA      899
Tyr Val Asp Glu Lys Ala Pro Glu Phe Ser Met Gln Gly Leu
                255             260

AAA TAA                                                      905
Lys
265
```

SOLUBLE VARIANTS OF TYPE I MEMBRANE PROTEINS, AND METHODS OF USING THEM

This is divisional of U.S. patent application Ser. No. 08/148,216, filed Nov. 5, 1993, now abandoned which is a continuation of U.S. patent application Ser. No. 07/778,232, filed Oct. 18, 1991, now abandoned.

This work was performed under grants CA 10815 and CA21124-1 from the National Institutes of Health.

FIELD OF THE INVENTION

This invention relates to novel soluble variants of the type I membrane proteins and to methods for making and using them. More specifically this invention relates to membrane proteins, and to methods of making and using them in the diagnosis and treatment of cancer.

BACKGROUND OF THE INVENTION

The GA733-2 antigen has been found to be associated with a variety of human carcinomas such as colorectal, pancreatic, and breast carcinoma [D. Herlyn et al, *J. Immunol. Meth.*, 73:157–167 (1984); H. G. Gottlinger et al, *Int. J. Cancer*, 38:47–53 (1986)].

GA733-2 is a 40 kDa human cell surface glycoprotein antigen that is associated with carcinomas of various origins. Its biological function remains unknown. Hydrophobicity analysis of the protein sequence predicted by cDNA has suggested that the GA733-2 antigen is a type I membrane protein, i.e., it possess signal peptide, extracellular domain, trans-membrane domain and intracellular anchor. An amino-terminal 23 residue signal peptide is followed by a 242 residue extracellular domain containing 12 cysteine residues and 3 potential N-glycosylation loci, a 23 residue trans-membrane domain, and a highly charged 26 residue intracellular anchor [S. Szala et al, *Proc. Natl. Acad. Sci, (USA)*, 87:3542–3546 (1990); see also, M. S. Perez and L. E. Walker, *Journal of Immunology*, 142:3662–67 (1989); J. Strnad et al, *Cancer Res.*, 49:314–17 (1989); and B. Simon et al, *Proc. Natl. Acad. Sci. (USA)*, 87:2755–59 (1990].

GA733-2 is a monoclonal antibody (mAb) defined antigen [A. H. Ross et al, *Biochem. Biophys. Res. Comm.*, 135:297–303 (1986)]. Several independently derived mAbs GA733, CO17-1A, M77, M79, 323/A3, among others, all define the GA733-2 antigen [See, for example, D. Herlyn et al, *J. Immuno. Methods*, 73:157–176 (1984), M. Herlyn et al, *Proc. Natl. Acad. Sci. (USA)*, 75:1438–1482 (1979) and M. Herlyn et al, *Hybridoma*, 5:S3-S10 (1986) for discussion of CO17-1A; H. G. Gottlinger et al, supra, for discussing of M77 and M79; and D. P Edwards et al, *Cancer Res.*, 48:1306–1317 (1986) for discussion of 323/A3].

Monoclonal antibodies that define tumor cell surface antigens are often being evaluated for the diagnosis and immunotherapy of cancer. Initial studies of mAbs CO17-1A and GA733 have demonstrated both cytotoxic effects in vitro and tumoricidal responses in vivo in experimental animal models. Clinical trials have shown strong mAb tumor binding [D. Herlyn et al, "Initial Clinical Evaluation of Two Murine Monoclonal Antibodies for Immunotherapy of Gastrointestinal Carcinoma," *Am. J. Clin. Oncol.*, (in press) (1991)]. Cases of partial and complete regression of disseminated cancer have also been reported [H. F. Sears et al, *J. Biol. Resp. Mod.*, 3:138–150 (1984); and J. E. Frodin et al, *Hybridoma*, 7:309–321 (1988)]. Since only microgram quantities of the native antigen are available, therapeutic approaches to date have been limited to passive immunization with mAb and active immunization with anti-idiotype mAb (A2).

Molecular clones for the GA733-2 antigen have been isolated by immunoselection of COS cells transfected with a cDNA expression library derived from a human colon carcinoma cell line [S. Szala et al, *Proc. Natl. Acad. Sci. (USA)*, 87:3542–3546 (1990)]. The GA733-2 sequence is identical to independently isolated cDNAs encoding the adenocarcinoma-associated antigen [J. Strand et al, *Cancer Res.*, 49:314–317 (1989); and M. E. Perez and L. E. Walker, *J. Immun.*, 142:3662–3667 (1989)]and the epithelial glycoprotein antigen [B. Simon et al, *Proc. Natl. Acad. Sci. (USA)*, 87:2755–2759 (1990)]. The GA733-2 coding region is 54% identical to the GA733-1 gene, a retroposon that is abundantly transcribed in pancreatic carcinoma cell lines [A. J. Linnenbach et al, *Proc. Natl. Acad. Sci. (USA)*, 86:27–31 (1989)]. The GA733-2 chromosomal gene contains exons encoding a epidermal growth factor-like repeat and an thyroglobulin type I repeat [A. J. Linnenbach, unpublished observation).

To date, other human tumor-associated antigens have been expressed in the vaccinia virus vector system: the epithelial tumor antigen expressed by breast carcinomas [M. Hareuveni et al, *Proc. Natl. Acad. Sci. (USA)*, 87:9498–9502 (1990)]; and the melanoma-associated glycoprotein p97 [C. D. Estin et al, *Proc. Nat. Acad. Sci. (USA)*, 85:1052–1056 (1988); and C. D. Estin et al, *J. Natl. Cancer Inst.*, 81:445–448 (1989)].

Recombinant p97 antigen has induced specific humoral, cellular, and protective immunity in mice, and humoral and cellular immunity in monkeys. These observations emphasize the potential usefulness of a recombinant human tumor-associated antigen as vaccines for cancer patients.

Furthermore, the preparative isolation of secretable protein domains containing a specific region of interest (i.e., eptiopes) which can be used in biological, immunological, or physical (i.e., crystallography) assays, implies extended possibilities for studying the nature and function of other membrane proteins.

The baculovirus-insect cell expression system has been well recognized for its ability to abundantly express recombinant proteins which most often resemble native protein with respect to function, immunoreactivity, and immunogenicity. Baculovirus has been exploited for production of a variety of enzymes, trans-membrane proteins, and secretory proteins such as tissue plasminogen activator, interleukin-2, and human beta interferon. A soluble variant of the cell surface protein CD4 has been generated by expressing a restriction enzyme cleaved portion of the CD4 cDNA [R. E. Hussey et al, *Nature (Lond.)*, 331:78–81 (1988)].

There remains a need in the art for an easily obtained and purified peptide which has the antigenicity of the GA733-2 membrane protein antigen in order to pursue immunological, physical and biochemical studies of this membrane protein, and to provide a means for diagnosis and immunotherapy against cancer.

SUMMARY OF THE INVENTION

In one aspect the present invention provides a polypeptide, designated GA733-2E. This polypeptide is a encoded by a truncated, modified version of native GA733-2 DNA, and permits secretion of an immunogenic fragment of the native GA733-2 antigen into the culture medium. This novel GA733-2E truncated antigen surprisingly retains the immunoreactivity and immunogenicity of the native full length GA733-2 antigen, and advantageously, may be easily purified from the culture medium into which it is secreted.

A further aspect of this invention is a pharmaceutical composition comprising GA733-2E as an active ingredient together with at least one substance selected from conventional pharmaceutical carriers, diluents, excipients and adjuvants. Optionally, GA733-2E may also be admixed with other active ingredients, including other GA733-2 variant peptides and other, known, cancer treating compounds. This composition may be used to elicit an immune response in a subject in a vaccine formulation. This composition is particularly useful in the treatment of various cancers.

Another aspect of this invention involves a method of eliciting a protective immune response in patients to certain tumors bearing a GA733-2 antigen by administering an effective amount of the a polypeptide and/or pharmaceutical composition described above. Such carcinomas include, but are not limited to, colorectal, pancreatic and breast carcinomas.

In yet another aspect, this invention provides diagnostic reagents, which include either the GA733-2E polypeptide or polynucleotide sequence, which sequence may be optionally associated with a detectable label, or bound to a solid support.

Thus still a further aspect of the invention are methods for diagnosing carcinomas which are characterized by the expression of native GA733-2antigen, which methods employ the recombinant GA733-2 polypeptide or polynucleotide sequences of the invention. Thus, the present invention provides a diagnostic kit for the detection of native GA733-2 antigen containing these diagnostic reagents.

Further, the invention provides the recombinant polypeptide GA733-2E, which may be used as a reagent for diagnostic purposes, and in methods for purifying and isolating the native antigen GA733-2.

In still another aspect, the invention provides a method of making soluble variants of GA733-2 proteins by omitting native GA733-2 DNA sequences for the trans-membrane and cytoplasmic domains, and creating a secretory protein from the extracellular domain. Preferably, this is accomplished via polymerase chain reaction (PCR).

Another aspect includes obtaining a soluble variant of any type I membrane protein produced by the method of omitting the DNA sequences for the transmembrane and cytoplasmic domains from the DNA sequence of said type I membrane protein. This truncated DNA sequence may then be produced by culturing a selected host cell transfect with a truncated DNA sequence in operative association with a regulatory sequence capable of directing the expression of the soluble variant. The soluble variant may also be produced by conventional synthesis.

Other aspects and advantages of the present invention are described further in the following detailed description of preferred embodiments of the present invention.

DETAILED DESCRIPTION OF THE INVENTION

The present invention provides novel soluble variants of a Type I membrane protein and methods for their preparation and use. Particularly exemplified in the following discussion of the invention are novel polypeptides characterized by the immunogenicity of naturally occurring Type I membrane protein, the GA733-2 tumor-associated antigen [see, Szala et al, Biochem., 87:3544 (1990), incorporated herein by reference]. However, it is to be understood that the methods applied to produce the GA733-2 variant proteins and polypeptides, and compositions and methods utilizing them, may also be applied to other Type I membrane proteins of particular interest.

Figure 1:
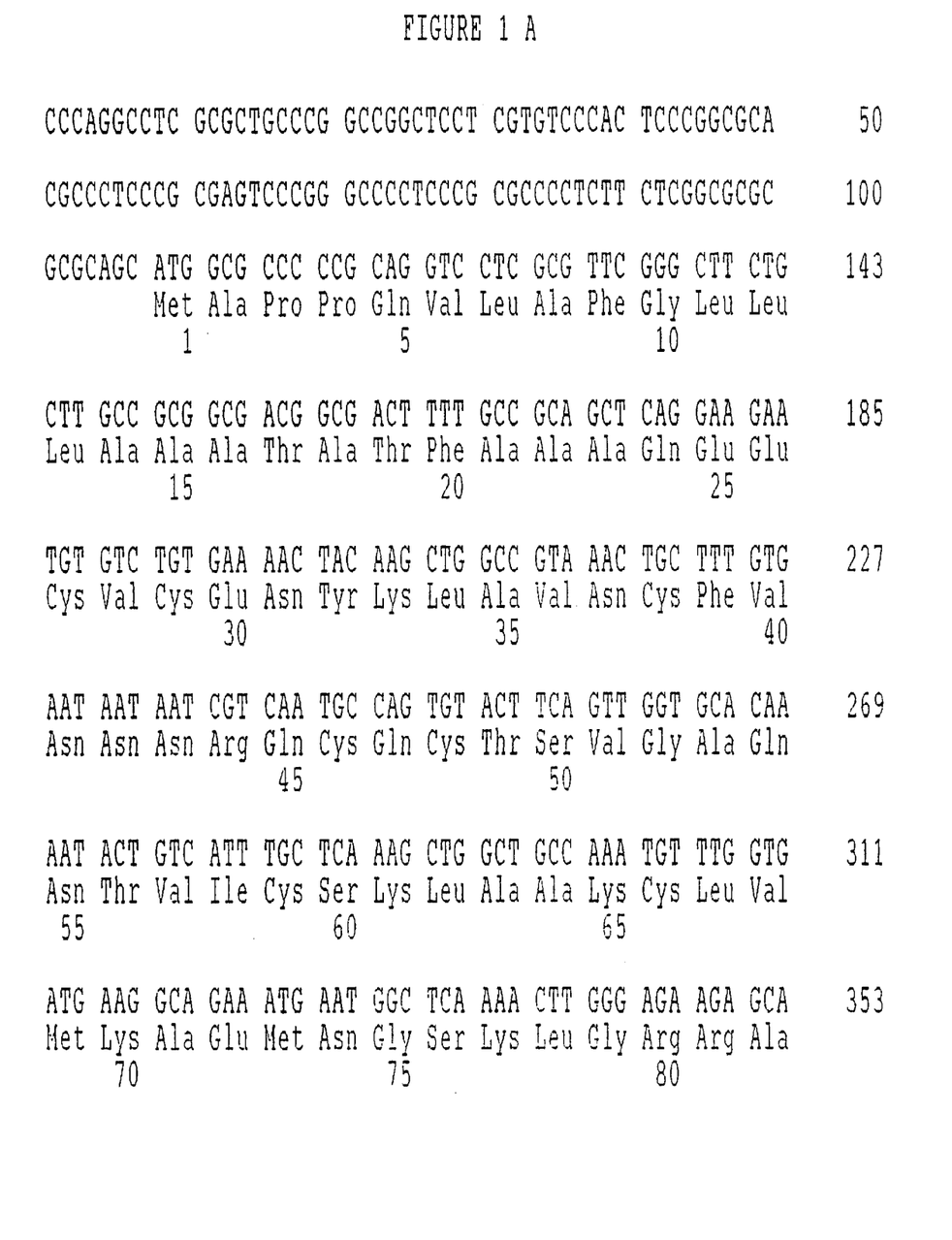
FIG. 1 illustrates the DNA and amino acid sequences of the truncated GA733-2E soluble variant of the invention [SEQ ID NO: 1 and 2].

One presently preferred polypeptide of the invention is designated GA733-2E. As illustrated in FIG. 1 [SEQ ID NO:1 and 2], GA733-2E is a truncated protein comprising the amino acids 1 through 265 of native GA733-2 [Szala et al, cited above]. As described in detail below in the examples, GA733-2E was prepared from the GA733-2 antigen, using PCR to delete the sequences for the transmembrane and cytoplasmic domains from the native GA733-2 antigen, thereby converting the extracellular domain into a secretory protein.

It has been demonstrated that this truncated polypeptide maintains the antigenicity of native GA733-2. This characteristic is particularly surprising because the recombinant GA733-2E is much smaller than native GA733-2, lacking the 3' terminal 189 nucleotides of native GA733-2 DNA (encoding 49 amino acids from the carboxy terminal of native GA733-2 protein).

The secreted recombinant antigen preparation described herein meets an important pre-clinical criteria for a potential vaccine, namely, the ability to elicit antibodies which can bind to human colorectal carcinoma cells. Both native GA733-2 and recombinant antigen GA733-2E elicited antibodies in mice which specifically and significantly bound to colorectal carcinoma cells at serum dilutions as high as 1:204,800.

It is anticipated that one of skill in the art may modify the GA733-2E polypeptide to enable expression of other soluble and secreted variants. For example, using the techniques described herein as well as known mutagenic techniques, one may alter one or more amino acids of the GA733-2E sequence, or to add or delete one or more additional amino acids from the amino or carboxy termini, while retaining the GA733-2 immunogenicity. Additionally, replacement of amino acids, e.g., conservative amino acid replacements, may be used to alter the sequence.

Conservative amino acid replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a major effect on its activity.

Such minor modifications to the polypeptide which permit the retention of the GA733-2 immunogenicity are believed to be encompassed by this invention.

The present invention also encompasses polynucleotide sequences, preferably DNA sequences, which encode the polypeptides described herein and sequences complementary thereto. A complementary sequence includes a contiguous sequence of nucleotides capable of selectively hybridizing to native GA733-2 or a complement thereof. The GA733-2E nucleotide sequence is reported in FIG. 1 [SEQ ID NO: 1], and contains the triplet TAA, encoding a stop codon, inserted immediately after the lysine-encoding codon at nucleotide number #902 [See FIG. 1]. The presence of this inserted stop codon deletes from the native GA733-2 nucleotide sequence both the trans-membrane and cytoplasmic domains, that is, the sequence encoding the 49 amino acid carboxy terminus of native GA733-2. Advantageously expression of this sequence in a selected host cell system allows facile secretion of the immunogenic GA733-2E polypeptide into the culture medium.

Polynucleotide sequences of this invention also include modified GA733-2E sequences, which modifications may be due to allelic variations (naturally-occurring base changes in the species population which may or may not result in an amino acid change). Similarly, modified DNA sequences which contain substantially the above described deletion and which code for the antigenic portion of native GA733-2 are also included in this invention. Such modified DNA sequences include those which differ in codon sequence due to the degeneracies of the genetic code, as well as variations in the modified DNA sequence encoding the antigenic portion of native GA733-2 which are caused by point mutations or by induced mutations to enhance the activity, half-life or production of the peptide encoded thereby. Such modifications may include additional nucleotide deletions or additions at the 5' and 3' termini. Typically, such modified polynucleotide sequences differ by only 1 to about 4 codon changes.

Other examples of DNA analogs include DNA sequences containing the above deletion and encoding a GA733-2E polypeptide with minor amino acid variations from the natural amino acid sequence of GA733-2; in particular, conservative amino acid replacements.

Utilizing the sequence data, it is within the skill of the art to obtain other DNA sequences encoding GA733-2E. For example, the gene may be manipulated by varying individual nucleotides, while retaining the correct amino acid(s), or varying the nucleotides, so as to modify the amino acids, without loss of antigenicity.

The polypeptides of the present invention are prepared preferably through use of conventional recombinant, genetic engineering techniques known to one of skill in the art. See, e.g., Sambrook et al, "Molecular Cloning. A Laboratory Manual.", 2d edition, Cold Spring Harbor Laboratory, Cold Spring Harbor, N.Y. (1989). Similarly useful in preparing polypeptides of this invention is the polymerase chain reaction (PCR) technique and known modifications thereof [See, e.g., Saiki et al, *Science,* 239:487 (1988)]. It is also possible to produce polypeptides of this invention by resort to chemical synthesis of overlapping polymers. These and other techniques described below are within the skill of the art.

The polypeptides of the present invention may be obtained by applying PCR technology to native GA733-2, a type I membrane protein, to obtain a secretable variant of that protein. As described in the examples below, the positioning of the 3' oligonucleotide primer for the PCR synthesis of the extracellular domain of the GA733-2 antigen is determined by hydrophobicity analysis, which located a 23 amino acid hydrophobic domain flanked by positively charged residues. This region was interpreted as representing the transmembrane domain. Once the truncated GA733-2E antigen is prepared by PCR, it may be incorporated into a selected vector for expression in a recombinant expression system as described below.

One method for producing the polypeptide of the invention recombinant, involves introducing the truncated polypeptide, e.g. GA733-2E, into a eukaryotic expression vector to make an expression system for the recombinant polypeptide. Non-eukaryotic expression systems are not desirable because proper folding is not obtained. A selected host cell is transformed with the vector and cultured. The method of this invention therefore comprises culturing a suitable eukaryotic cell or cell line, which has been transformed with a DNA sequence coding for expression of a polypeptide characterized by the immunogenicity of native, purified GA733-2 under the control of known regulatory sequences.

Suitable host cells or cell lines for expression of the recombinant polypeptides of this invention may include insect cells, mammalian cells, yeast cells or other fungal cells. The selection of suitable mammalian host cells and methods for transformation, culture, amplification, screening and product production and purification are known in the art. See e.g., Gething and Sambrook, *Nature,* 293:620–625 (1981), or alternatively, Kaufman et al, *Mol. Cell. Biol.,* 5(5):1750–1759 (1985) or Howley et al, U.S. Pat. No. 4,419,446. Normal diploid cells, cell strains derived from in vitro culture of primary tissue, as well as primary explants, are suitable. Candidate cells may be genotypically deficient in the selection gene, or may contain a dominantly acting selection gene. Suitable mammalian cell lines include, but are not limited to, Chinese Hamster ovary cells (CHO), HeLa, mouse L-929 cells, 3T3 lines derived from Swiss, Balb-c or NIH mice, BHK or HaK hamster cell lines, monkey COS-1 cell lines and the CV-1 cell line.

Many strains of yeast and other fungal cells known to those skilled in the art are also available as host cells for expression of the polypeptides of the present invention. However, insect cells are currently the preferred host cells in the method of the invention. See e.g., Miller et al, *Genetic Engineering,* 8:277–298 (Plenum Press 1986) and references cited therein. Suitable insect expression systems, of both the lytic and non-lytic type, are well known to those of skill in the art. For example, baculovirus cell expression systems are commercially available from sources such as Invitrogen [San Diego, Calif.]. Techniques for expression using such systems are also known to those skilled in the art. [See, e.g., Summers and Smith, *Texas Agricultural Experiment Station Bulletin No.* 1555 (1987)]. Further, it is contemplated that the use of a non-lytic baculovirus system, such as that described by D. Jarvis et al, *J. Biotech.,* 8:1950 (1990), may be advantageous in producing the recombinant polypeptide of the invention.

The present invention also provides recombinant molecules or vectors for use in the method of expression of the novel GA733-2E polypeptide and other polypeptides of this invention. These vectors contain the DNA sequence, e.g., the GA733-2E DNA sequences, illustrated in FIG. 1 [SEQ ID NO:1 and 2], which alone or in combination with other sequences, encodes an immunogenic fragment of GA733-2.

The vector employed in the method also contains selected regulatory sequences in operative association with the DNA coding sequences of the invention. These regulatory sequences are capable of directing the replication and expression of the DNA coding sequences in selected host cells. Regulatory sequences include promoter fragments, terminator fragments and other suitable sequences which direct the expression of the protein in an appropriate host cell. One of skill in the art may select from among known regulatory sequences depending upon the selected host cell to be used in expressing the polypeptides of this invention.

Appropriate expression vectors of which numerous types are known in the art for mammalian, fungal, and preferably insect, expression can also be selected by one of skill in the art for this purpose.

Once expressed in a selected host cell system, the resulting polypeptide is desirably secreted into the cell culture. Because the polypeptides of this invention share immunoreactivity and immunogenicity with the native antigen, antibodies to the native antigen may be utilized to isolate the recombinant GA733-2E from the culture medium by conventional methods. The examples below provide a purification scheme for isolating the soluble protein from the culture medium.

In an embodiment of this invention, GA733-2E DNA was cloned into the baculovirus transfer vector pVL1392 [Invitrogen Corp., San Diego, Calif.] and introduced into Autographa californica nuclear polyhidrosis virus by homologous recombination. Spodoptera frugiperda (Sf9) cells infected with the GA733-2E DNA baculovirus recombinant abundantly secreted a 31 kDa glycoprotein into the culture medium. Recombinant secretory antigen displayed an in vitro immunoreactivity to mAb and an in vivo immunogenicity in mice that were similar to native antigen.

The GA733-2E recombinant antigen produced by Sf9 insect cells resembles the native antigen produced by human cells in several reports. The GA733-2E recombinant antigen undergoes N-linked glycosylation and is immunoreactive to anti-GA733-2 monoclonal antibodies (mAb) in vitro. As determined in either immunoblotting or enzyme linked immunosorbent assay (ELISA), the recombinant antigen reacts with a group of four mAbs defining three different epitopes (GA733, CO17-1A; and M77/M79).

The applicability of this approach, i.e., modification via PCR to remove the trans-membrane and cytoplasmic domains, expression in a selected host cell system and purification from culture supernatants, to other type I membrane proteins will be a function of the accuracy of locating their trans-membrane domains. One advantage of this system in the production of recombinant soluble Type I membrane protein variants is that detergent-free, recombinant antigen can be purified from serum-free culture media by mAb affinity column chromatography, preferably in one purification step. Thus, a recombinant protein or polypeptide characterized by the immunogenicity of the native antigen can be obtained without the necessity of extensive culturing of human carcinoma cell lines and laborious extraction procedures.

The method for recombinant expression described herein may also be employed to express recombinant GA733-2, which recombinant protein is referred to in the examples below as GA733-2F. Recombinant GA733-2F which is characterized by the entire amino acid sequence of the native antigen is expressed within the cell. Therefore isolation of this recombinant antigen differs from that of GA733-2E in that the full length recombinant antigen is not secreted from the cell and must be obtained from the cell lysate by conventional means. However, in all other respects, the presently described method of production of GA733-2E may be employed to obtain recombinant GA733-2F.

The polypeptides described herein and produced by the methods described above may be used in therapeutic, vaccinal and pharmaceutical compositions to elicit an active immune response in a subject. For example, the protective effects of injections with the GA733-2F antigen may be evaluated using an animal tumor model. Thus, the antigens of this invention are desirable for use in vaccine compositions.

These polypeptides are particularly useful in the treatment and immunization for various cancers. The active immunotherapy of cancer with purified tumor-associated antigens requires that antigen DNA be molecularly cloned and expressed, since these antigens cannot be purified in sufficient quantities from cultured human tumor cells. The therapeutic mechanism of the compositions and methods of the present invention differs in principle from that of the large majority of drugs for treatment of carcinoma in use at the present time. The immunogens of the present invention display highly specific activity in generating active immunity against the tumors, so that patients do not suffer the many disadvantages of conventional cancer therapy. Alternatively, the recombinant antigen of the invention may be used in combination with known tumoricidal agents. The tumors susceptible to treatment or immunization by the present method and compositions include, but are not limited to, colorectal, pancreatic, and breast carcinomas. Other tumor types which express GA733-2 can be identified by various methods known in the art.

The pharmaceutical and vaccinal compositions of the invention comprise a therapeutically effective amount of a polypeptide of this invention in admixture with a pharmaceutically acceptable carrier. The pharmaceutical compositions may be utilized in conventional type formulations such as, particularly, injectables.

In one embodiment of this invention, the therapeutic and pharmaceutical compositions of the invention may include GA733-2E polypeptide in admixture with an adjuvant. Suitable adjuvants are well known to those of skill in the art and include saponins such as Quil A, aluminum hydroxide, lipid A (particularly when incorporated into a liposome carrier), bacillus calmette guerin (BCG), glucan, and combination products, such as DETOX [Ribi Immunochemical Research, Inc., Hamilton, Mont.]. DETOX contains detoxified endotoxin (monophosphoryl lipid A), cell wall skeletons of Mycobacterium, and squalene. This product has recently been reported to be particularly useful for use in cancer patients. [Mitchell et al, *Cancer Res.*, 48:5883 (1988)]. Optionally, these compositions may also include other modified GA733-2 polypeptides.

It is further contemplated that pharmaceutical and vaccinal compositions containing GA733-2E as active immunogen may also contain immunomodulators such as cytokines, including interleukins and interferons. Suitable immunomodulatory dosages can be readily determined by one of skill in the art. When these agents are combined in a pharmaceutical composition with the type I membrane antigen variants of this invention, it is anticipated that each active ingredient will be present in the combined composition in the same concentration or slightly lower concentration than if the active ingredient was administered alone.

Suitable carriers are well known to those of skill in the art of pharmacology [see, e.g., Remingtons Practice of Pharmacy, 9th, 10th and 11th Ed.]. To a large extent, selection of the carrier depends upon the adjuvant selected. For example, if aluminum hydroxide or glucan is selected as the adjuvant, sterile saline would be an appropriate carrier; if BCG is the adjuvant, an oil would be appropriate carrier. Therefore, exemplary carriers may include sterile saline, lactose, sucrose, calcium phosphate, gelatin, dextrin, agar, pectin, peanut oil, olive oil, sesame oil, squalene and water. The pharmaceutical compositions of the invention may also be administered via liposomes according to known techniques. In addition, dependent upon the adjuvant selected, e.g. BCG, the carrier or diluent may include a time delay material, such as glyceryl monosterate or glyceryl distearate alone or with a wax.

The formulations of the pharmaceutical composition containing the polypeptides of this invention may conveniently be presented in unit dosage form and may be prepared by any of the conventional methods. Alternatively, the composition may be in a form adapted for slow release in vivo, as is known in the art. All methods include the steps of brining into association the active ingredient with the carrier which may constitute one or more accessory ingredients.

The pharmaceutical and vaccinal compositions of this invention, e.g., containing the GA733-2E as the active material, may be used as a immunotherapeutic. These compositions may be administered parenterally, or by other appropriate routes. The parenteral route is presently preferred and compositions may be prepared by dissolving the compound in a suitable solvent such as an aqueous buffer and dimethyl sulfoxide or glycerol. The parenteral route may be intramuscular, intravenous, intradermal, or subcutaneous.

The concentration of the novel peptides, e.g., the recombinant, modified GA733-2 antigens, in combination with a pharmaceutical carrier can be determined by the attending physician, taking into consideration various factors. These factors, which may modify the action of drugs, include e.g. the condition, body weight, sex and diet of the patient, the severity of the tumor, time of administration and other clinical factors. The dosage of the compositions of the invention used to treat or immunize against the specific disease condition described herein may be varied depending on the particular disease and the sate of the disease. Generally, the daily regimen should be in the range of about 1 μg to about 1000 mg of GA733-2E polypeptide, or analogs thereof, and preferably 0.01 to about 100 mg per kg body weight of a subject. A desirable dosage regimen may involve administration of one to three doses of the vaccine composition, where the antigenic content of the composition is as stated above.

In addition to vaccinal or therapeutic use for the human disorders described herein, the methods and compositions of this invention may be utilized for veterinary purposes in the treatment of, or immunization of an animal against, carcinomas that afflict other mammals, including horses, swine and cattle, and fowl, for example. These disorders may be treated using similar vaccinal and therapeutic quantities of the polypeptides of this invention that may be used in treating the disorders described hereinabove.

The polypeptides of the present invention may also be used for diagnostic, as well as therapeutic, purposes. According to the method of the present invention, where desired, primary tumor tissue from a patient can be assayed for GA733-2 expression prior to treatment using a polypeptide of this invention. For example, antibodies to native GA733-2 antigen which are present in patient serum may be detected in vitro by reaction with a polypeptide of the present invention. In situ hybridization may also be an effective method of diagnosis. Other means of ascertaining tumor expression of GA733-2 surface antigen are known and may be used in order to ascertain the probable effectiveness of immunotherapy with the polypeptides described herein.

A polypeptide of this invention, e.g., GA733-2E, may be used in a competitive immunoassay with labelled antibodies to GA733-2. One such competitive assay involves the use of unlabelled GA733-2E polypeptides which are bound to a solid surface, such as latex particles or a dipstick. A labelled antibody is incubated with either a standard antigen or a tissue sample and is then put in contact with the solid surface. The GA733-2E antigen competes with the native GA733-2 antigen for binding to the labelled antibody. In the absence of any native antigen in the tissue sample, a visual label appears. Expression of GA733-2 on the tumor cell surface would be indicated by the absence of a detectable label.

In another known system, the monoclonal antibody is bound to a solid surface. The solid phase is then incubated with a standard, e.g., unlabelled GA733-2E polypeptide, or with a test sample. Labelled GA733-2E polypeptide is then placed in contact with solid surface. The absence of a detectable label indicates that the sample expressed GA733-2 antigen.

In yet another aspect, the polypeptide of the invention, or monoclonal antibodies directed thereto, could be adapted for use in commercially available assay systems, such as the double determinant test kits which are commercially available. Briefly, this involves the use of two monoclonal antibodies, each directed to a different antigenic determinant. A MAb to a first antigenic determinant is bound to the solid surface, which is then incubated with either standard purified antigen, e.g., the GA733-2E polypeptide of this invention, or a tissue extract sample. A labelled MAb to a second antigenic determinant is then added to the plate.

When the GA733-2E polypeptide is used as a reagent in competitive immunoassay, detectable labels for attachment to the polypeptide may be easily selected by one skilled in the part of diagnostic assays. Labels detectable visually are often preferred for use in diagnostic kits and in clinical applications due to the rapidity of the signal and its easy readability. For colorimetric detection, a variety of enzyme systems have been described in the art which will operate appropriately in the homogenous assay. As one example of enzyme 1, glucose oxidase, which uses glucose as a substrate, may be employed. Interaction between glucose and glucose oxidase releases peroxide as a product. Enzyme 2 may therefore be peroxidase, which reacts with peroxide and a hydrogen donor such as tetramethyl benzidine (TMB) producing an oxidized TMB that is seen as a blue color.

In the assay employing colorimetric enzyme systems, such as horseradish peroxidase (HRP) or alkaline phosphatase (AP), the reaction should be read within approximately 5 to 15 minutes, preferably 10 minutes, to obtain an accurate result. A longer reaction time can lead to color changes induced by trace amounts of enzyme remaining on the reaction surface. Where desirable, a "stop" solution can be employed to disable the enzyme from further reaction after the above 5 to 15 minutes period. It is known, for example, that sulfuric acid may be added to stop the reaction of HRP.

Other such proximal enzyme systems are known to those of skill in the art, including hexokinase in conjunction with glucose-6-phosphate dehydrogenase which reacts with ATP, glucose, and NAD+ to yield, among other products, NADH that is detected as increased absorbance at 340 nm wavelength. The loss of absorbance at 340 nm wavelength by the oxidation of NADH is another indicator of positive results in either allosteric activation using phosphofructokinase in conjunction with phosphoenol pyruvate carboxylase and substrates fructose-6-phosphate and NADH or allosteric inhibition using aspartate aminotransferase in conjunction with phosphoenol pyruvate carboxylase and substrates oxalacetate, glutamate and NADH. Also, bioluminescence of chemiluminescence can be detected using, respectively, NAD oxidoreductase with luciferase and substrates NADH and FMN or peroxidase with luminol and substrate peroxide.

Other label systems that may be utilized in the methods of this invention are detectable by other means. For example, one desirable method employs colored latex microparticles, such as those marketed by Bangs Laboratories of Indiana. These latex particles in which is embedded a dye may be used in place of enzymes to form conjugates with the antibodies and recombinant GA733-2E of the invention and provide a visual signal indicative of the presence of the resulting antibody-antigen complex in applicable assays. The use of such particles eliminates the need for subsequent substrate addition steps, and avoids enzyme and substrate reagent instability.

Other conventional label systems that may be employed include fluorescent compounds, radioactive other appropriate label systems are known to those of skill in the art. The selection of a detectable label or label system is merely conventional. Similarly a wide variety of solid supports are available to the art, such as latex beads. Selection of solid supports and the association thereof with polypeptides of this invention are also considered conventional.

The methods and polypeptides described herein may be effectively utilized in the assembly of a diagnostic kit. Such a diagnostic kit contains the components necessary to practice one or more of the assays described above (or other conventional assay systems) for the expression of GA733-2 surface antigen on tumor cells. Thus, the homogeneous assays the kit may contain a monoclonal antibody directed to a native GA733-2, which Mab is associated with a first enzyme, a vial for containing the urine sample, and the synthetic GA733-2E polypeptide conjugated to the second enzyme, which in proximity to the first enzyme, produces a visible product. Other conventional components of such diagnostic kits may also be included.

Alternatively, a kit may contain a monoclonal antibody specific for GA733-2 antigen bound to a solid surface and associated with a first enzyme, the synthetic GA733-2E polypeptide associated with a second enzyme, and a sufficient amount of the substrate for the first enzyme, which, when added to the tumor sample and reagents, provides the reactant for the second enzyme, resulting in the color change in the absence of native GA733-2. For an agglutination assay kit, the latex beads would be bound to the monoclonal antibodies generated against synthetic GA733-2E polypeptide.

Where the detectable label present in association with the antibody is designed for non-visual detection, e.g., for radioimmunoassay, the standard components necessary for this assay, e.g., controls, standards and the like, are included in the kit. In the diagnostic kits of this invention, reagents are included which define a clear cut end to the color development step, such as the stop solutions described above.

In order that the invention described herein may be more fully understood, the following examples are set forth. It should be understood that these examples are for illustrative purposes only, and should not be construed as limiting this invention in any way.

EXAMPLE 1

PCR Synthesis of GA733-2 Extracellular Domain

Oligonucleotide primers were designed for PCR synthesis of a truncated cDNA that encodes the amino-terminal signal peptide sequence and the extracellular 242 amino acids of the selected antigen, GA733-2 [R. K. Saiki et al, "Enzymatic Amplification of β-globin Genomic Sequences and Restriction Site Analysis for Diagnosis of Sickle Cell Anemia," *Science*, 230:1350–1354 (1985)].

Oligonucleotide primers were synthesized by automated phosphoramidite chemistry on a model 380A DNA synthesizer [Applied Biosystems]. PCR synthesis was performed with GA733-2 cDNA template (1 ng) [S. Szala et al, cited above], oligonucleotide primers (1 µM each), and *Thermus aquaticus* polymerase in a volume of 100 µl.

The oligonucleotide primers are as follows: Primer 1 [SEQ ID NO:3], which corresponds to nucleotides 85–114 of native GA733-2 DNA (sense strand)

5'-CCTCTTCTCGGCCTGCAGGCAGCATGGCGC-3'
and Primer 2 [SEQ ID NO:4], which corresponds to nucleotides 885–919 of native GA733-2 DNA (antisense strand)

5'-AGTTACGTCCCAGATTTTATTAGATCTTAACG ACA-3'.

Primer 1 contains a Pst I restriction enzyme site (CTGCAG), which was placed 11 bp upstream of the inherent initiation codon (ATG). The positioning of primer 1 considerably reduces the GC-rich 5' untranslated sequences, which are thought to impair the translational level of the recombinant product [M. D. Summers et al, "A Manual of Methods for Baculovirus Vectors and Insect Cell Culture Procedures," *Texas Agricultural Experiment Station Bulletin*, No. 1555 (1988)]. At the 3' end, Primer 2 introduced a termination codon, TAA (ATT in the antisense strand), in place of the first amino acid of the putative hydrophobic trans-membrane domain [S. Szala et al]. Additionally, Primer 2 placed an Xba I restriction site (AGATCT) immediately adjacent to the stop codon.

PCR was carried out for 35 cycles (denaturing at 94° C. for 1 minute, annealing at 40° C. for 2 minutes, elongation at 72° C. for 3 minutes) by using the DNA Thermal Cycler [Perkin Elmer Cetus, Norwalk, Ct.]. The final elongation step was extended by 7 minutes. The reaction was extracted with phenol/chloroform and the DNA was purified by glass bead adsorption [Bio 101, Inc., La Jolla, Calif.]. PCR products were analyzed in ethidium bromide-stained agarose gels (2% Nusieve, 1% Seakem) [FMC Bio Products, Rockland, Me.] and the expected ~800 bp cDNA band was visualized.

This PCR-synthesized, truncated version of the cDNA is termed GA733-2E [SEQ ID NO:1 and 2].

EXAMPLE 2

Preparation of GA733-2E Baculovirus Recombinants

Figure 2:
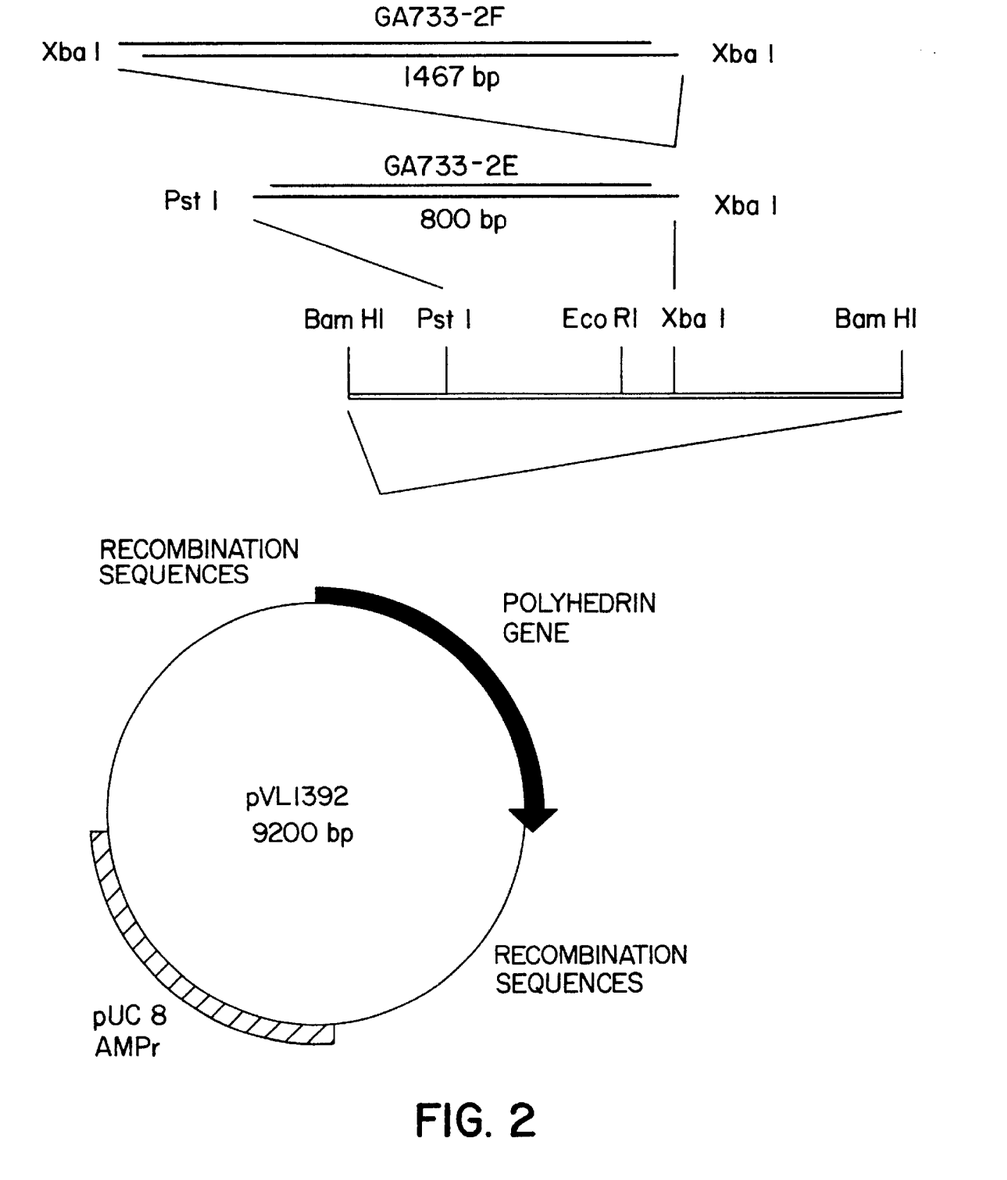
FIG. 2 depicts the construction of baculovirus transfer vectors for recombinant GA733-2F and GA733-2E.

The construction of a baculovirus transfer vector for GA733-2E [SEQ ID NO:1 and 2], is depicted in FIG. 2. In order to compare expression of our truncated recombinant, we also constructed a recombinant containing the full length version of GA733-2. This recombinant was designated GA733-2F, also shown in FIG. 2. GA733-2F was derived by digesting the CDM8 recombinant plasmid with Xba I at 37° C. for 1 hour [S. Szala et al, supra]. The reaction was stopped by the addition of sodium dodecyl sulfate (SDS) to 0.1% and extracted with phenol/chloroform. The GA733-2F full-length cDNA was inserted into the Xba I site of the baculovirus transfer vector pVL1392 [Invitrogen Corp., San Diego, Calif.], downstream of the AcNPV polyhedrin promoter. The restriction enzymes Pst I and Xba I were used to subclone the GA733-2E PCR product into pVL1392. Optimal conditions for the ligation of GA733-2E to Xba I digested pVL1392 with T4-ligase [Boehringer-Mannheim, F.R.G.] were an insert:vector molar ratio of 3:1 and a total concentration of 5' ends of 0.4 µM (4.36 µg DNA/10 µl).

The ligated product was transformed into competent DH5α E. coli cells, and insert-containing clones were identified by bacterial colony hybridization [M. Grunstein et al, "Colony Hybridization; a Method for the Isolation of Cloned DNAs that Contain a Specific Gene," *PNAS* (*USA*), 72:3961–3965 (1975)].

The GA733-2E PCR product (Example 1) was digested with Pst I and Xba I. Directional cloning into pVL1392 was carried out by using an insert:vector molar ratio of 3:1 and a total concentration of 5' ends of 0.03 µM (390 ng DNA/10 µl). Recombinant pGA733-2E was isolated and the insert was sequenced to monitor the fidelity of the PCR synthesis.

Although *T. aquaticus* polymerase is known to produce misincorporations, DNA sequence analysis of the pVL1392-2E recombinant containing the PCR-derived insert indicated 100% identity to the native GA733-2 cDNA sequence [R. K. Saiki et al, *Science*, 239:487–491 (1988)]. Since homologous recombination between the recombinant plasmid transfer vectors and the baculovirus genome is a very rare event, two rounds of enrichment for recombinant virus by dot-blot hybridization (an autoradiography of lysed insect cell microcultures dot-blotted to nitrocellulose membranes and probed with $^{32}$P-labelled GA733-2 cDNA) preceded 1–2 rounds of visual screening for occlusion body negative recombinant viral plaques. For example, in the second dot-blot hybridization screening for GA733-2F, well number F10 was found to be plaque pure on first round of visual screening. The GA733-2E recombinant [SEQ ID NO:1 and 2] was purified in the same manner.

EXAMPLE 3

Generation and Purification of Baculovirus Recombinants

Sf9 *Spodoptera frugiperda* insect cells [Invitrogen, Corp., San Diego, Calif.] were cultured at 27° C. in supplemented Grace's Insect Medium [Gibco, Gaithersburg, Md.] containing 10% fetal bovine serum (FBS) and antibiotics. An aliquot of 1.5×10$^6$ cells was co-transfected with 2 µg of CaCl purified pGA733-2F or pGA733-2E, respectively, and 1 µg of purified AcNPV viral DNA, by using the calcium chloride precipitation method [M. D. Summers et al, supra]. After 7 days of incubation, a viral stock containing wild-type and recombinant viruses was harvested.

Recombinants were enriched by two rounds of dot-blot hybridization screening [M.-C. Fung et al, *J. Virol. Meth.*, 19:33–42 (1988)]. Fifty µl of serially diluted viral supernatant (10$^{-2}$–10$^{-8}$, first round; 10$^{-3}$–10$^{-7}$, second round) were used to infect 1.5×10$^4$ cells in each well of a 96-well plate. Supernatants were collected 6 days post infection (p.i.). Cells were lysed in 0.2 N NaOH, vacuum blotted onto nitrocellulose filters [Schleicher & Schuell, Keene, N.H.], and hybridized to a nick translated, $^{32}$P-labelled GA733-2 cDNA insert probe (1×10$^6$ counts/ml). Supernatants containing recombinant virus were indicated by autoradiography of the filters.

Plaque purification was carried out by 1–2 rounds of visual screening of infected Sf9 cell monolayers with 0.75% agarose overlay [Seakem, FMC Bio Products, Rockland, Me.]. Occlusion body negative plaques, representing pure recombinant viral colonies were picked 7 days p.i. Agarose plugs were eluted in culture medium that was used to infect 2×10$^6$ Sf9 cell monolayers in 25 ml culture flasks, yielding 5 ml of pure high-titer viral stock supernatants (2–5×10$^8$ plaque-forming unit/ml).

EXAMPLE 4

Expression of Recombinant Antigens

Aliquots of 2×10$^6$ Sf9 cells in mid-logarithmic growth phase (99% viable) were infected with the GA733-2E viral recombinant including a wild type AcNPV virus control obtained from Invitrogen (Maxbac™) at a multiplicity of infection of at least 10. In the baculovirus life cycle, protein production regularly reaches a maximum 48 to 72 hours p.i. Recombinant protein was therefore harvested 64 hours p.i. The first 24 hours of incubation proceeded in TNM-FH medium, i.e., supplemented Grace's insect medium, obtained from Invitrogen. The cells were then cultured for 40 hours under serum-free conditions (Sf900 medium) [Gibco, Gaithersburg, Md.]. Supernatants were collected and cell pellets were extracted with a buffer containing nonidet P-40 (0.5% NP-40, 0.14 M NaCl, 0.01 M NaF, 0.01 M Tris (pH 7.5), 5 mM EDTA, 1 mM phenylmethylsufonyl-fluoride and 8 µg/ml aprotinin). Sf9 cell lysates were clarified by centrifugation at 100,000×g. Cell lysates were prepared from positive control, colorectal carcinoma SW948 cells [ATCC CCL 237] in the same manner.

The purification procedure was conducted as follows: (1) BSA and GA733 Ab columns were equilibrated with 20 mM Tris (Sigma T-1503) buffer, pH 7.5 ("wash buffer"); (2) the filtered solution was passed through the BSA column; (3) the BSA column flow-through was passed through the GA-733 Ab column; (4) the column was washed with wash buffer and the wash was collected; (5) the antigen was eluted from the column with 50 mM diethyl amine buffer, pH11 ("elution buffer"), and each of the 10 1 ml fractions was neutralized with 1 M TRIS, pH 6 ("neutralization buffer"); (6) the column was washed again with 20–30 mls wash buffer and the wash was collected.

We performed a Western blot using the wash from step (1), the flow-through from step (2), the wash from step (4), the eluate from step (5), and the wash from step (6). We then pooled the tubes containing the antigen according to the results of the Western blot. We dialyzed the antigen eluate against PBS, using 3500 MW cutoff dialysis tubing and determined protein concentration by Lowry protein assay. The antigen was then ready for testing in radioimmunoassay or ELISA.

Fifth µg of protein (Lowry) from supernatants or detergent extracts were boiled for 90 seconds in non-reducing loading buffer [2% SDS, 62.5 mM Tris-Cl (pH 6.8), 10% glycerol, 0.001% bromphenol blue] prior to electrophoresis in a 15% SDS-polyacrylamide gel [U. K. Laemmli, *Nature* (*Lond.*), 227:680–685 (1970)]. Samples were electro-blotted onto nitrocellulose filters (BioRad, Richmond, Calif.) and reacted with the murine mAb GA733 (1 µg/ml) [described in D. Herlyn et al, *J. Immuno. Methods*, 73:157–167 (1984)]. Antibody binding to the recombinant proteins was visualized through an alkaline phosphatase conjugated anti-mouse immunoglobulin G (IgG) [Promega, Madison, Wis.].

Sf9 insect cells infected with GA733-2F and GA733-2E purified recombinant virus were found by immunoblot analysis to be capable of expressing recombinant antigens carrying the epitope defined by mAb GA733. Additional immunoblot experiments established that the recombinant antigen has a second epitope defined by mAb M77 and M79 [H. G. Gottlinger et al, *Int. J. Cancer*, 38:47–53 (1986)].

Reactivity with mAb 323/A3 [D. P. Edwards et al, *Cancer Res.*, 46:1306–1317 (1986)] was also observed.

Detergent extracts of cells infected with GA733-2F baculovirus exhibited antigen that appeared heterogeneous in size (34, 37, 40, 44 and 76 kDa), with the major 40 kDa species co-migrating with the native glycoprotein expressed by SW948 colorectal carcinoma cells. Sf9 control cells infected with wild-type AcNPV produced no protein bound by mAb GA733. The high $M_r$ species (76 kDa) seen in FA733-2F infected cells may represent an antigen dimer. The antigen expression level of GA733-2F was not significantly affected by its 5' GC-rich untranslated sequence, in comparison to GA733-2E which lacks these sequences. In comparison to cell lysates, the supernatants of GA733-2F infected cells showed recombinant 40 kDa protein in low amount, probably resulting from cell shearing and cell death during the course of infection, liberating protein from the membranes to the supernatant medium.

As was seen with the GA733-2F antigen, multiple species of the GA733-2E antigen [SEQ ID NO:1 and 2] are also apparent. The detergent extract of cells infected with GA733-2E baculovirus has minor (29, 35 kDa) and a major (31 kDa) monomeric species, and possible dimer (62 kDa) and tetramer (112 kDa) species. As anticipated, the GA733-2E baculovirus infected cells exhibited a greater amount of antigen in the culture supernatant, compared to recombinants containing the full length version of GA733-2 (GA733-2F). The GA733-2E antigen [SEQ ID NO:1 and 2] found in the supernatant appears less heterogeneous, with the 31 kDa species predominating. Thus, by removing sequences for the transmembrane and cytoplasmic domains, we converted a type I membrane protein into a secreted protein.

EXAMPLE 5

N-Glycosylation of Recombinant Antigens

Antigen heterogeneity was studied by culturing infected Sf9 cells in the presence of two different concentrations of tunicamycin. We carried out this N-glycosylation inhibition study for the recombinant GA733-2E antigen [SEQ ID NO: 1 and 2]. Cells were seeded and infected as described above. After 24 hours of incubation, TMH-FH medium was replaced by serum-free Sf900 medium containing 2 $\mu$g/ml or 5 $\mu$g/ml of the N-glycosylation inhibitor tunicamycin [R. T. Schwarz et al, *TIBS*, 5:65–67 (1980)]. After a total incubation time of 64 hours, protein was harvested from the supernatant and from lysed cells as described earlier. Electrophoresis and immunoblotting was carried out as described above with forty $\mu$g of protein was applied to each lane.

Immunoblot analysis with mAb GA733 demonstrated a more uniform appearance of both GA733-2E [SEQ ID NO: 1 and 2] and GA733-2F recombinant antigens. N-linked glycosylation appeared to have been blocked almost entirely at concentrations of 2 g/ml of tunicamycin.

The diversity of subspecies around the major 40 kDa antigen species of GA733-2F was reduced to a predominant 34 kDa species. This is in agreement with the antigen's calculated protein molecular mass of 34.9 kDa [S. Szala et al, cited above]. Faint additional bands can possibly be attributed to the minimal residual N-glycosylation permitted by the concentrations of tunicamycin administered to the Sf9 cells. The 76 kDa putative antigen dimer was found to be reduced to 63 kDa by tunicamycin.

The major 31 kDa form of GA733-2E [SEQ ID NO: 1 and 2] was reduced to a 29 kDa species, which is consistent with a protein molecular mass of 29.8 kDa calculated from the truncated cDNA sequence. The putative 62 kDa antigen dimer was reduced to 55 kDa. Hence, the diversity of subspecies of both recombinant antigens found in the immunoblot analysis are the result of different stages of the insect cell's glycosylation process and do not represent different protein primary structures.

EXAMPLE 6

Immunoreactivities of Native and Secreted Recombinant Antigens

Secretory GA733-2E was used for further immunological studies and compared with native GA733-2. mAb affinity chromatography of supernatants from large-scale Sf9 cell suspension cultures infected with GA733-2E baculovirus yields an average of ~1.0 mg of secreted antigen per liter. The full-length recombinant GA733-2F antigen [SEQ ID NO:1 and 2] was not further analyzed.

SW1116 colorectal carcinoma cells and WM9 melanoma cells have previously been described [H. Koprowski et al, *Somat. Cell Genet.*, 5:957–972 (1979); and M. Herlyn et al, *Cancer Invest.*, 1:215–224 (1983)]. Native GA733-2 antigen was obtained from NP-40 lysate of SW1116 tumors grown in nude mice. Detergent extracts were purified on mAb GA733 immunoaffinity columns as described previously [A. H. Ross et al, *Biochem. Biophys. Res. Comm.*, 135:297–303 (1986)].

For large-scale production of secreted recombinant antigen, Sf9 cells were infected with GA733-2E recombinant baculovirus at a multiplicity of infection of 5. The cells were cultivated at 27° C. in spinner flasks at $2 \times 10^6$ cells/ml in TNM-FH medium for 24 hours, and then in serum-free Sf900 medium for an additional 40 hours. The infected Sf9 cell culture supernatants were harvested by centrifugation and passed over a mAb GA733 immunoaffinity column.

Female Balb/c mice, 16 weeks old (Harlan Sprague-Dawley, Indianapolis, Ind.), were immunized s.c. 3 times, at 2 week intervals, with 1 to 5 $\mu$g of aluminum hydroxide precipitated [D. Herlyn et al, *Proc. Natl. Acad. Sci (USA)*, 84:8055–8059 (1987)] native GA733-2 antigen, secreted recombinant GA733-2E antigen, or bovine serum albumin (BSA). Mouse sera were obtained before and at 24, 38, 50 and 70 days following the first immunization.

Binding of mAb CO17-1A and GA733 to purified tumor antigen was determined in ELISA as previously described [M. Wettendorff et al, *J. Immunol. Method.*, 116:105–115 (1989)]. Wells of microtiter plates were coated with various concentrations (0.2–5 $\mu$g/ml) of antigen or BSA. Binding of mAb or normal mouse IgG (0.4–10 $\mu$g/ml) was detected by alkaline phosphatase conjugated goat anti-mouse F(ab')$_2$ antibody [Cappel Labs, Durham, N.C.] and substrate. Optical densities were measured at 405 nm in a Titertek ELISA reader [ICN Biomedicals, Inc., Costa Mesa, Calif.].

Binding of mouse sera to GA733-2 antigen-positive SW1116 cells and antigen-negative melanoma cells WM9 was determined in mixed hemadsorption assay as previously described [D. Herlyn et al, "Anti-idiotypic Antibodies Bear the Internal Image of a Human Tumor Antigen," Science, 232:100–102 (1986)].

Adherent tumor cells were incubated with various dilutions of mouse sera obtained before and after immunization with native GA733-2 antigen, recombinant GA733-2E antigen [SEQ ID NO:1 and 2], or BSA. Binding of serum antibodies to the cells was detected by sheep red blood cells that had been bound with mouse anti-sheep red blood cell antibodies and rabbit anti-mouse IgG antibodies serving as indicator cells. Statistical significance of immunological data was calculated with Student's t-test.

Figure 3:
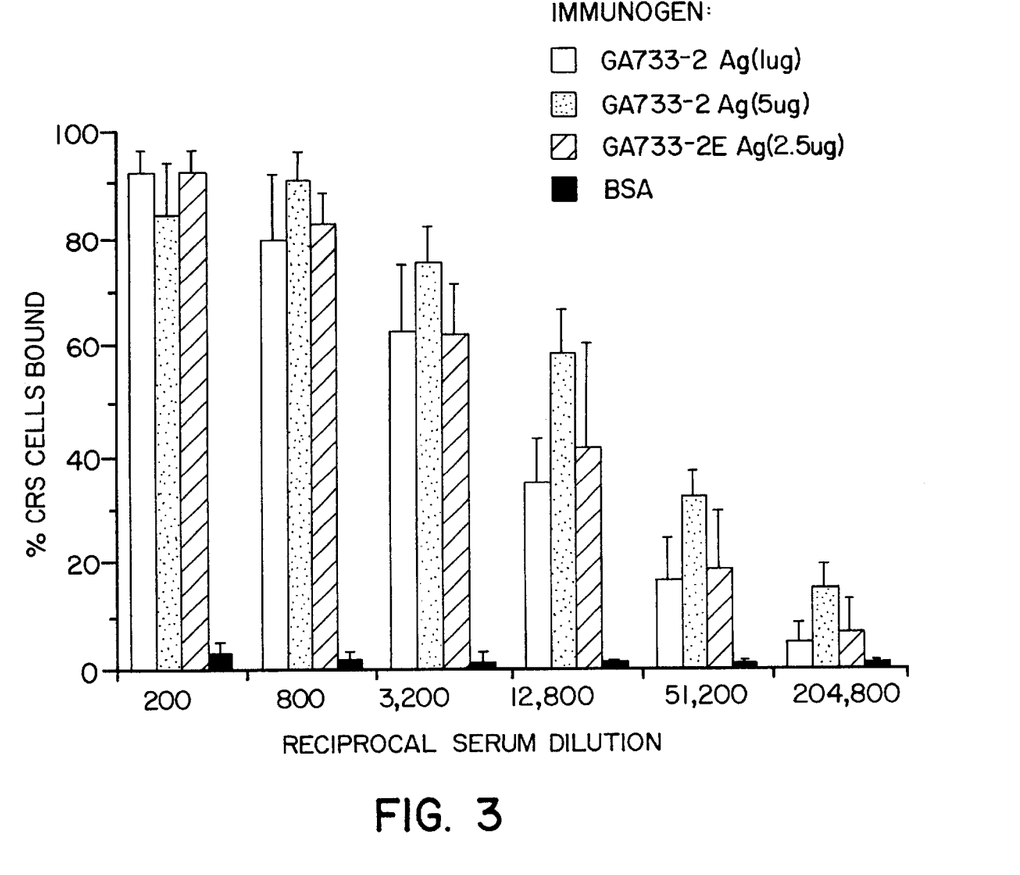
FIG. 3 demonstrates the immunogenicity of secreted recombinant antigen GA733-2E vs. GA733-2 and a control bovine serum albumin (BSA).

Referring to FIG. 3, on day 50 of the experiment (i.e., 22 days after the final immunization) both the native GA733-2 antigen and the recombinant GA733-2E antigen induced antibodies binding to antigen-positive SW1116 colorectal carcinoma cells were observed. No binding to antigen-negative melanoma cells WM9 was observed. Such antibodies were not induced by immunizations with BSA (FIG. 3). The serum end point dilutions (i.e., the highest dilutions of experimental sera showing significant (P<0.05) binding versus control sera obtained either before antigen or after BSA immunization) were similar (~1:204,800) for both groups immunized with either native GA733-2 antigen (1 µg/injection) or recombinant GA733-2E antigen (2.5 µg/injection) (FIG. 3) [SEQ ID NO:1 and 2].

Furthermore, both antigen preparations induced similar (P>0.05) concentrations of anti-colorectal carcinoma cell antibodies at all serum dilutions tested. Concentrations of colorectal carcinoma cell-binding antibodies induced with native GA733-2 antigen were somewhat dependent on the dose of the administered antigen (1 µg dose<5 µg dose, P<0.05, at serum dilutions of 12.8, 51.2, and $204.8 \times 10^{-3}$). Hence, as is often the case with proteins expressed in the baculovirus system, the immunogenicity of recombinant and native antigens are similar [V. A. Luckow et al, Biotechnology, 6:47–55 (1988)].

Maximal binding reactivities of mAb CO17-1A [M. Herlyn et al, Hybridoma, 5:S3–S10 (1986)] and mAb GA733 to native GA733-2 antigen, recombinant GA733-2E antigen [SEQ ID NO:1 and 2], or BSA (negative control) are shown in Table 1, below:

TABLE 1

Immunoreactivities of Native and Secreted Recombinant Antigens
Binding of mAb to purified native (GA733-2) and recombinant (GA733-2E) antigens were determined by ELISA.

| | Maximal optical density (at 405 nm) of antibody binding to antigen[a] | | |
|---|---|---|---|
| Antibdy[b] | GA733-2 | GA733-2E | BSA |
| CO17-1A | 0.60 | 1.21 | 0.07 |
| GA733 | 0.86 | 1.30 | 0.02 |
| Normal mouse IgG | 0 | 0 | 0 |

[a]All values were corrected for buffer contros; target antigens at 5 µg/ml.
[b]At 10 µg/ml of antibody.

Both mAb specifically bound to native and recombinant antigen preparations, as indicated by the absence of binding of either mAb to BSA, or of normal mouse IgG to tumor antigen. mAb binding to either of the two GA733-2 antigen preparations was both mAb and antigen concentration-dependent.

Recombinant GA733-2E antigen [SEQ ID NO:1 and 2] showed significantly higher (P<0.05) binding reactivity then the native GA733-2 antigen. This was consistent with 2 different batches of each antigen. This phenomenon may be related to the different methods used in the preparative isolation of native membrane antigen and secreted recombinant antigen. Both the immunoblot and ELISA data indicated that the processes of antigen truncation and expression in insect cells yielded a recombinant antigen with epitopes recognized by mAb raised against native antigen.

While certain embodiments of the invention have been particularly described, it will be apparent to those skilled in the art that many modifications and variations may be made. Therefore, the present invention is not to be construed as limited by any of the particular embodiments shown, rather its scope will be defined only by the claims which follow.

What is claimed is:

1. A pharmaceutically acceptable composition for treatment of cancer which comprises immunogenic GA733-2E consisting of the amino acid sequence of SEQ ID NO: 2, and at least one other cancer treating compound in a pharmaceutically acceptable carrier.

2. A pharmaceutically acceptable composition which comprises immunogenic GA733-2E consisting of the amino acid sequence of SEQ ID NO: 2, and an immunomodulator in a pharmaceutically acceptable carrier.

3. A composition according to claim 2, wherein the immunomodulator is a cytokine selected from the group consisting of an interleukin and an interferon.

4. A pharmaceutically acceptable composition which comprises immunogenic GA733-2E consisting of the amino acid sequence of SEQ ID NO: 2, in a pharmaceutically acceptable carrier, wherein said carrier is a liposome.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 905 base pairs
      (B) TYPE: nucleic acid
      (C) STRANDEDNESS: double
      (D) TOPOLOGY: unknown    (ii) MOLECULE TYPE: DNA (genomic)

(ix) FEATURE:
      (A) NAME/KEY: CDS
      (B) LOCATION: 108..902

(xi) SEQUENCE DESCRIPTION: SEQ ID NO:1:

CCCAGGCCTC GCGCTGCCCG GCCGGCTCCT CGTGTCCCAC TCCCGGCGCA CGCCCTCCCG    60

```
CGAGTCCCGG GCCCCTCCCG CGCCCCTCTT CTCGGCGCGC GCGCAGC ATG GCG CCC      116
                                                    Met Ala Pro
                                                      1

CCG CAG GTC CTC GCG TTC GGG CTT CTG CTT GCC GCG GCG ACG GCG ACT      164
Pro Gln Val Leu Ala Phe Gly Leu Leu Leu Ala Ala Ala Thr Ala Thr
         5                  10                  15

TTT GCC GCA GCT CAG GAA GAA TGT GTC TGT GAA AAC TAC AAG CTG GCC      212
Phe Ala Ala Ala Gln Glu Glu Cys Val Cys Glu Asn Tyr Lys Leu Ala
 20              25                  30                      35

GTA AAC TGC TTT GTG AAT AAT AAT CGT CAA TGC CAG TGT ACT TCA GTT      260
Val Asn Cys Phe Val Asn Asn Asn Arg Gln Cys Gln Cys Thr Ser Val
                 40                  45                  50

GGT GCA CAA AAT ACT GTC ATT TGC TCA AAG CTG GCT GCC AAA TGT TTG      308
Gly Ala Gln Asn Thr Val Ile Cys Ser Lys Leu Ala Ala Lys Cys Leu
             55                  60                  65

GTG ATG AAG GCA GAA ATG AAT GGC TCA AAA CTT GGG AGA AGA GCA AAA      356
Val Met Lys Ala Glu Met Asn Gly Ser Lys Leu Gly Arg Arg Ala Lys
         70                  75                  80

CCT GAA GGG GCC CTC CAG AAC AAT GAT GGG CTT TAT GAT CCT GAC TGC      404
Pro Glu Gly Ala Leu Gln Asn Asn Asp Gly Leu Tyr Asp Pro Asp Cys
     85                  90                  95

GAT GAG AGC GGG CTC TTT AAG GCC AAG CAG TGC AAC GGC ACC TCC ACG      452
Asp Glu Ser Gly Leu Phe Lys Ala Lys Gln Cys Asn Gly Thr Ser Thr
100             105                 110                 115

TGC TGG TGT GTG AAC ACT GCT GGG GTC AGA AGA ACA GAC AAG GAC ACT      500
Cys Trp Cys Val Asn Thr Ala Gly Val Arg Arg Thr Asp Lys Asp Thr
                120                 125                 130

GAA ATA ACC TGC TCT GAG CGA GTG AGA ACC TAC TGG ATC ATC ATT GAA      548
Glu Ile Thr Cys Ser Glu Arg Val Arg Thr Tyr Trp Ile Ile Ile Glu
             135                 140                 145

CTA AAA CAC AAA GCA AGA GAA AAA CCT TAT GAT AGT AAA AGT TTG CGG      596
Leu Lys His Lys Ala Arg Glu Lys Pro Tyr Asp Ser Lys Ser Leu Arg
         150                 155                 160

ACT GCA CTT CAG AAG GAG ATC ACA ACG CGT TAT CAA CTG GAT CCA AAA      644
Thr Ala Leu Gln Lys Glu Ile Thr Thr Arg Tyr Gln Leu Asp Pro Lys
     165                 170                 175

TTT ATC ACG AGT ATT TTG TAT GAG AAT AAT GTT ATC ACT ATT GAT CTG      692
Phe Ile Thr Ser Ile Leu Tyr Glu Asn Asn Val Ile Thr Ile Asp Leu
180                 185                 190                 195

GTT CAA AAT TCT TCT CAA AAA ACT CAG AAT GAT GTG GAC ATA GCT GAT      740
Val Gln Asn Ser Ser Gln Lys Thr Gln Asn Asp Val Asp Ile Ala Asp
                200                 205                 210

GTG GCT TAT TAT TTT GAA AAA GAT GTT AAA GGT GAA TCC TTG TTT CAT      788
Val Ala Tyr Tyr Phe Glu Lys Asp Val Lys Gly Glu Ser Leu Phe His
             215                 220                 225

TCT AAG AAA ATG GAC CTG ACA GTA AAT GGG GAA CAA CTG GAT CTG GAT      836
Ser Lys Lys Met Asp Leu Thr Val Asn Gly Glu Gln Leu Asp Leu Asp
         230                 235                 240

CCT GGT CAA ACT TTA ATT TAT TAT GTT GAT GAA AAA GCA CCT GAA TTC      884
Pro Gly Gln Thr Leu Ile Tyr Tyr Val Asp Glu Lys Ala Pro Glu Phe
     245                 250                 255

TCA ATG CAG GGT CTA AAA TAA                                          905
Ser Met Gln Gly Leu Lys
260             265
```

(2) INFORMATION FOR SEQ ID NO:2:

(i) SEQUENCE CHARACTERISTICS:
        (A) LENGTH: 265 amino acids
        (B) TYPE: amino acid (D) TOPOLOGY: linear (ii) MOLECULE TYPE: protein (xi) SEQUENCE DESCRIPTION: SEQ ID NO:2:

Met Ala Pro Pro Gln Val Leu Ala Phe Gly Leu Leu Leu Ala Ala Ala
 1               5                  10                  15

Thr Ala Thr Phe Ala Ala Ala Gln Glu Glu Cys Val Cys Glu Asn Tyr
                20                  25                  30

Lys Leu Ala Val Asn Cys Phe Val Asn Asn Arg Gln Cys Gln Cys
             35                  40                  45

Thr Ser Val Gly Ala Gln Asn Thr Val Ile Cys Ser Lys Leu Ala Ala
         50                  55                  60

Lys Cys Leu Val Met Lys Ala Glu Met Asn Gly Ser Lys Leu Gly Arg
 65                  70                  75                  80

Arg Ala Lys Pro Glu Gly Ala Leu Gln Asn Asn Asp Gly Leu Tyr Asp
                 85                  90                  95

Pro Asp Cys Asp Glu Ser Gly Leu Phe Lys Ala Lys Gln Cys Asn Gly
                100                 105                 110

Thr Ser Thr Cys Trp Cys Val Asn Thr Ala Gly Val Arg Arg Thr Asp
            115                 120                 125

Lys Asp Thr Glu Ile Thr Cys Ser Glu Arg Val Arg Thr Tyr Trp Ile
130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
                180                 185                 190

Ile Asp Leu Val Gln Asn Ser Ser Gln Lys Thr Gln Asn Asp Val Asp
            195                 200                 205

Ile Ala Asp Val Ala Tyr Tyr Phe Glu Lys Asp Val Lys Gly Glu Ser
210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys
                260                 265

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:3:

CCTCTTCTCG GCCTGCAGGC AGCATGGCGC                                30

(2) INFORMATION FOR SEQ ID NO:4:

(i) SEQUENCE CHARACTERISTICS:
        (A) LENGTH: 35 base pairs
        (B) TYPE: nucleic acid
        (C) STRANDEDNESS: unknown -continued

```
          (D) TOPOLOGY: unknown (ii) MOLECULE TYPE: DNA (genomic)

(xi) SEQUENCE DESCRIPTION: SEQ ID NO:4:

AGTTACGTCC CAGATTTTAT TAGATCTTAA CGACA                                              35
```